United States Patent [19]
Suchowsky, deceased et al.

[11] 3,948,890
[45] Apr. 6, 1976

[54] 4H-1,3-BENZOXAZIN-2-ONE-3-ACETOHYDROXAMIC ACID DERIVATIVES

[75] Inventors: Giselbert Karl Suchowsky, deceased, late of Milan, Italy, by Brunhilde Pasewald Suchowsky, sole heir; Luigi Bernardi, Milan, Italy; Severina Coda, Milan, Italy; Lorenzo Pegrassi, Milan, Italy

[73] Assignee: Farmitalia Societa Farmaceutica Italia, Milan, Italy

[22] Filed: Dec. 29, 1972

[21] Appl. No.: 319,724

[30] Foreign Application Priority Data
Dec. 28, 1971 Italy.................................. 32992/71

[52] U.S. Cl............................ 260/244 R; 424/248
[51] Int. Cl............................................ C07d 87/08
[58] Field of Search...................................... 260/244

[56] References Cited
OTHER PUBLICATIONS
Zayed et al., Archiv. Pharm., Vol. 303, pp. 933–938, (1970).

*Primary Examiner*—Harry I. Moatz
*Attorney, Agent, or Firm*—Hubbell, Cohen & Stiefel

[57] ABSTRACT
Compounds of the formula:

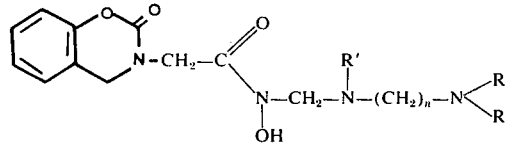

wherein R and R' are lower alkyl groups having from 1 to 4 carbon atoms, eventually substituted by a hydroxyl group; $n$ is an integer from 0 to 3 and R' together with the

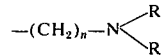

group jointly represent the group

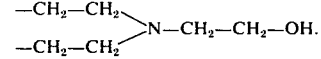

A process for the preparation of these compounds is also disclosed. The compounds of the invention display interesting pharmacological activities and may be usefully employed as antidepressants.

3 Claims, No Drawings

4H-1,3-BENZOXAZIN-2-ONE-3-ACETOHYDROXAMIC ACID DERIVATIVES

The present invention relates to 4H-1,3-benzoxazin-2-one-3-actohydroxamic acid derivatives and to a process for the preparation thereof. More particularly the invention relates to compounds of the formula:

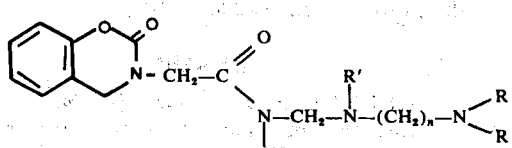

wherein
R and R' are lower alkyl groups having from 1 to 4 carbon atoms
n is an integer from 0 to 3 and
R' together with the

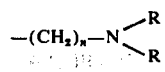

group jointly represent the group.

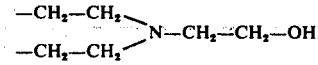

The compounds of the invention display interesting pharmacological activities and may be usefully employed as antidepressants.

The process for the preparation of the new 4H-1,3-benzoxazin-2-one-3-acetohydroxamic acid derivatives consists of condensing a suitable acid such as described in British Pat. No. 1,164,749 with formaldehyde and a suitable dibasic amine to give crystalline and stable derivatives, which are completely soluble in water, and which contain an equivalent of a weak acid, such as acetic, lactic and any physiologically compatible acid.

This process may be represented by the scheme:

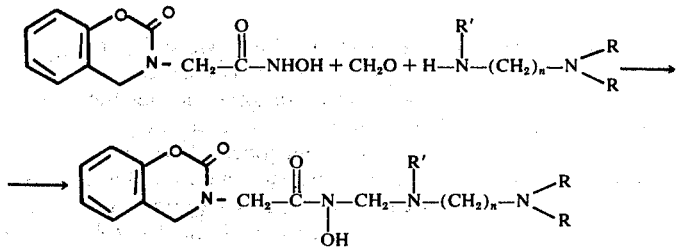

wherein R' and R are as defined above.

More particularly, 4H-1,3-benzoxazin-2-one-3-acetohydroxamic acid, suspended in a suitable solvent, e.g. ethanol, is admixed with formaldehyde and the desired dibasic amine. It is generally preferred to use a concentrated aqueous solution of formaldehyde. The mixture is allowed to stand at room temperature for from 10 minutes to 1 hour. The precipitated product is washed and recrystallized by conventional techniques.

The obtained compounds display very interesting pharmacological activities, such as preventing reserpine induced depression.

Among the compounds of the invention, 4H-1,3-benzoxazin-2-one-3-[N-($\beta$-hydroxyethyl)-piperazinomethyl]-acetohydroxamic acid has been particularly studied and compared with 4H-1,3-benzoxazin-2-one-3-acetohydroxamic acid. The former compound does not modify, up to dosages of 200 mg/kg i.v., spontaneous behavior, motor apparatus coordination, muscular tension or nociceptive reflexes in albino male mice (weight 20–22 g) for the period of observation (5 hours).

Table 1 gives the results of 4H-1,3-benzoxazin-2-one-3-[N-($\beta$-hydroxyethyl)-piperazino-methyl]-acetohydroxamic acid compared to 4H-1,3-benzoxazin-2-one-3-acetohydroxamic acid and to Imipramine, a commercially available antidepressant, with respect to the antagonism to the reserpine induced syndrome.

TABLE 1

| Compound | Doses mg/kg | Administration route | Ptosis | Rectal temperature in °C |
|---|---|---|---|---|
| Control | — | intraperitoneal | 0 | 37.9 |
| Reserpine (R) | 3.0 | intraperitoneal | 40 | 32.1 |
| Imipramine + R | 50.0 | intraperitoneal | 29 | 36.0 |
| 4H-1,3-benzoxazin-2-one-3-acetohydroxamic acid + R | 50.0 | intraperitoneal | 29 | 36.0 |
|  | 100.0 | intraperitoneal | 5 | 38.1 |
| 4H-1,3-benzoxazin-2-one-3-[N-($\beta$-hydroxyethyl)-piperazinomethyl]-aceto- | 25.0 | intraperitoneal | 24 | 33.1 |
|  | 50.0 | intraperitoneal | 19 | 35.6 |

TABLE 1-continued

| Compound | Doses mg/kg | Administration route | Ptosis | Rectal temperature in °C |
|---|---|---|---|---|
| hydroxamic acid + R | 100.0 | intraperitoneal | 2 | 37.6 |

Table 1 clearly shows that 4H-1,3-benzoxazin-2-one-3-[N-(β-hydroxyethyl)-piperazinomethyl]-acetohydroxamic acid is the most active in antagonizing the ptosis and the hypothermia induced by reserpine.

It is to be noted that an intraperitoneal dose of 50 mg/kg of Imipramine is the highest tolerated dose, while 4H-1,3-benzoxazin-2-one-3-[N-(β-hydroxyethyl)-piperazinomethyl]- acetohydroxamic acid is tolerated up to an intraperitoneal dose of 300 mg/kg.

The antireserpine effect of 4H-1,3-benzoxazin-2-one-3-[N-(β-hydroxyethyl)-piperazinomethyl]-acetohydroxamic acid in a behavior test is also shown in the swimming rat. While the reserpinized animals can no longer get out of a basin full of water, those pretreated with 4H-1,3-benzoxazin-2-one-3-[N-(β-hydroxyethyl)-piperazinomethyl]-acetohydroxamic acid plus reserpine manage to get out of the basin within a period of time slightly longer than that of the control animals.

TABLE 2

| Compound | Dose mg/kg intraperitoneal | Average time to get out of the basin (in seconds) | Number of the animals which do not get out |
|---|---|---|---|
| Controls | — | 13.1 | 0/10 |
| Reserpine (R) | 5 | — | 10/10 |
| Imipramine+R | 25 | 40 | 7/10 |
| 4H-1,3-benzoxazin-2-one-3-acetohydroxamic acid+R | 50 | 25 | 0/10 |
| 4H-1,3-benzoxazin-2-one-3-[N-(β-hydroxyethyl)-piperazinomethyl]-acetohydroxamic acid+R | 25 | 28 | 0/10 |

Table 2 shows the superiority of the product of the invention compared to the other tested products.

The acute toxicity (LD$_{50}$), determined on albino male mice (weight 20–22 g) by a single oral and intravenous administration, is settled within 48 hours.

TABLE 3

| Compound | LD$_{50}$ mg/kg per os | intravenous |
|---|---|---|
| Imipramine | 488 | 35 |
| 4H-1,3-benzoxazin-2-one-3-acetohydroxamic acid | ~2000 | 350 |
| 4H-1,3-benzoxazin-2-one-3-[N-(β-hydroxyethyl)-piperazinomethyl]-acetohydroxamic acid | >3000 | 576 |

Table 3 shows that 4H-1,3-benzoxazin-2-one-3-[N-(β-hydroxyethyl)-piperazinomethyl]-acetohydroxamic acid, administered by the intravenous route, is about half again less toxic than 4H-1,3-benzoxazin-2-one-3-acetohydroxamic acid and about 20 times less toxic than Imipramine.

The following examples illustrate the invention without limiting it.

EXAMPLE 1

4H-1,3-benzoxazin-2-one-3-[N-(β-hydroxyethyl)-piperazinomethyl]-acetohydroxamic acid. acid.

1 g of 4H-1,3-benzoxazin-2-one-3-acetohydroxamic acid (obtained in accordance with the dislosure in British Pat. No. 1,164,749), suspended in 7 cc of 99% ethanol, was admixed with 0.6 g of β-hydroxyethyl-piperazine, dissloved in 4 cc of ethanol and 0.4 cc of 38% formaldehyde. The mixture was stirred with shaking at room temperature. After 10–15 minutes, a solution was obtained from which a white crystalline precipitate was separated. Shaking was continued for about 1 hour more, the product was filtered and washed with alcohol/ether to yield 1.45 g of the compound melting at 166°–168°C. After recrystallization from 95% ethanol, the product melts at 168°–170°C.

EXAMPLE 2

4H-1,3-benzoxazin-2-one-3-[(N,N,N'triethyl)-ethylenediaminomethyl]-acetohydroxamic acid.

Operating as in Example 1, but employing as the dibasic amine N,N,N'-triethyl-ethylenediamino, 4H-1,3-benzoxazin-2-one-3-[(N,N,N'-thiethyl)-ethylendiaminomethyl]-acetohydroxamic acid, which melts at 82°–84°C, was obtained. The latter compound also gave good test results.

The data obtained for the compound described in this Example are as follows.

TABLE 4

| Dose mg/kg intraperitoneal | Average time to get out of the basin (in seconds) | Number of the animals which do not get out |
|---|---|---|
| 50 | 10 | 1/10 |

TABLE 5

| LD$_{50}$ mg/kg | |
|---|---|
| per os | intravenous |
| 2549 | 327.5 |

It is claimed:

1. A compound of the formula:

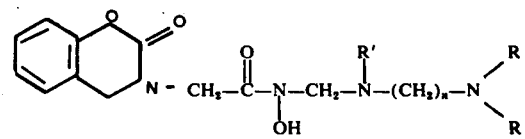

wherein R' and R are lower alkyl containing from 1 to 4 carbon atoms; n is an integer from 0 to 3; and R' together with the —(CH$_2$)$_n$—NR$_2$ group jointly represent the group

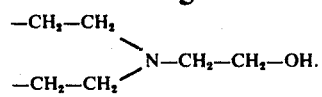
2. The compound of claim 1, which is 4H-1,3-benzoxazin-2-one-3-[N-(β-hydroxyethyl)-piperazinomethyl]-acetohydroxamic acid.
3. The compound of claim 1, which is 4H-1,3-benzoxazin-2-one-3-[(N,N,N'-triethyl)-ethylendiaminomethyl]-acetohydroxamic acid.
* * * * *

UNITED STATES PATENT OFFICE
CERTIFICATE OF CORRECTION

Patent No. 3,948,890               Dated   April 6, 1976

Inventor(s)  LUIGI BERNARDI et al

It is certified that error appears in the above-identified patent and that said Letters Patent are hereby corrected as shown below:

Title page, right side, lines 2-3: "1 to 4 carbon atoms, eventually substituted by a hydroxyl group; $\underline{n}$ is an integer from 0 to 3 and R' to-" should read -- 1 to 4 carbon atoms, $\underline{n}$ is an integer from 0 to 3 and R' to- --.

Column 1, line 20: "2-one-3-actohydroxamic" should read -- 2-one-3-acetohydroxamic --.

Column 4, line 12: "acid. acid" should read -- acid. --; line 33: "N,N,N'-triethyl-ethylenediamino," should read -- N,N,N'-triethyl-ethylendiamino, --; line 34: [(N,N,N'-thiethyl)" should read -- [(N,N,N'-triethyl) --.

Signed and Sealed this

Twenty-fourth Day of August 1976

[SEAL]

Attest:

RUTH C. MASON
*Attesting Officer*

C. MARSHALL DANN
*Commissioner of Patents and Trademarks*